US010736521B2

United States Patent
Bienek et al.

(10) Patent No.: US 10,736,521 B2
(45) Date of Patent: Aug. 11, 2020

(54) DEVICE AND METHOD FOR MONITORING AND DIAGNOSING THE AUTOREGULAR MECHANISM OF THE BLOOD PRESSURE OF A LIVING BEING

(71) Applicant: Schwarzer Cardiotek GmbH, Heilbronn (DE)

(72) Inventors: Carsten Bienek, Neuenstadt (DE); Michael Spaeth, Stuttgart (DE); Cornelius Fritz Vollmer, Obersulm (DE)

(73) Assignee: Schwarzer Cardiotek GmbH (DE)

( * ) Notice: Subject to any disclaimer, the term of this patent is extended or adjusted under 35 U.S.C. 154(b) by 251 days.

(21) Appl. No.: 15/736,334

(22) PCT Filed: Jul. 2, 2015

(86) PCT No.: PCT/EP2015/065129
§ 371 (c)(1),
(2) Date: May 22, 2018

(87) PCT Pub. No.: WO2017/001023
PCT Pub. Date: Jan. 5, 2017

(65) Prior Publication Data
US 2018/0249916 A1  Sep. 6, 2018

(51) Int. Cl.
*A61B 5/024* (2006.01)
*A61B 5/00* (2006.01)
(Continued)

(52) U.S. Cl.
CPC ........ *A61B 5/02405* (2013.01); *A61B 5/0245* (2013.01); *A61B 5/02108* (2013.01);
(Continued)

(58) Field of Classification Search
CPC ............ A61B 5/02405; A61B 5/02125; A61B 5/7246; A61B 5/02108
(Continued)

(56) References Cited

U.S. PATENT DOCUMENTS

| 7,163,512 B1 | 1/2007 | Childre et al. |
| 2006/0224073 A1* | 10/2006 | Lin ..................... A61B 5/02007 600/513 |
| 2007/0021675 A1* | 1/2007 | Childre .................. A61B 5/024 600/508 |

FOREIGN PATENT DOCUMENTS

WO   2005043628   5/2005

OTHER PUBLICATIONS

International Search Report dated Mar. 30, 2016.

* cited by examiner

*Primary Examiner* — Amanda K Hulbert
*Assistant Examiner* — Philip C Edwards
(74) *Attorney, Agent, or Firm* — Carlson, Gaskey & Olds, P.C.

(57) ABSTRACT

A method of monitoring and/or diagnosing an autoregulation mechanism of blood pressure of a living being using an ECG signal includes recording the ECG signal of the living being, and the recording a pulse wave curve synchronously with the recording of the ECG signal. Heart rate intervals are determined from the ECG signal. A pulse wave transit time is determined for each heart rate interval from the pulse wave curve. A plurality of significant changes in the pulse wave transit times are determined according to a specified criterion. One respective heart rate interval correlated in time with each significant change in the pulse wave transit times is selected as an anchor point. A determined limited number of temporally successive heart rate intervals temporally before and/or after each anchor point are selected to
(Continued)

thus generate a limited sequence of heart rate intervals for each anchor point. The method further includes averaging the corresponding heart rate intervals of each sequence of a respective anchor point over all sequences of the anchor points.

20 Claims, 8 Drawing Sheets

(51) Int. Cl.
*A61B 5/021* (2006.01)
*A61B 5/0245* (2006.01)
*A61B 5/0432* (2006.01)
*A61B 18/00* (2006.01)
*A61B 18/14* (2006.01)
*A61B 5/026* (2006.01)

(52) U.S. Cl.
CPC ........ *A61B 5/02125* (2013.01); *A61B 5/0432* (2013.01); *A61B 5/4035* (2013.01); *A61B 5/7239* (2013.01); *A61B 5/7246* (2013.01); *A61B 5/026* (2013.01); *A61B 5/7285* (2013.01); *A61B 18/1492* (2013.01); *A61B 2018/00404* (2013.01); *A61B 2018/00434* (2013.01); *A61B 2018/00511* (2013.01); *A61B 2018/00577* (2013.01)

(58) Field of Classification Search
USPC ........................................ 600/509
See application file for complete search history.

DEVICE AND METHOD FOR MONITORING AND DIAGNOSING THE AUTOREGULAR MECHANISM OF THE BLOOD PRESSURE OF A LIVING BEING

FIELD OF THE INVENTION

The invention relates to a device and to a method of monitoring and/or measuring the autoregulation mechanism of the blood pressure of living beings.

BACKGROUND

The autoregulation mechanisms of the blood pressure of human beings, for example, ensure that the cardiovascular system reacts in an appropriate manner to sudden blood pressure variations (change in position, injury, etc.) such that physical damages due to too high or too low blood pressure are avoided.

Due to the measurement of this autoregulation, it is possible to draw conclusions about the autonomous control of the cardiovascular activity. Applications are for example in the risk assessment of cardiovascular diseases. Specifically the risk of a sudden cardiac death seams to be directly connected to the vagal control of the cardiovascular system.

A method of measuring the autoregulation consists in the measurement of the baroreflex system feedback. In the baroreflex regulation mechanism, the blood pressure is monitored via baroreceptors in the aortic arch and the carotids, and signals are forwarded to the vegetative nervous system in case of an increase or decrease in blood pressure. When the blood pressure increases, the sympathetic nervous system is dampened, and the parasympathetic nervous system is activated. This leads, among others, to a decrease in the heart rate and to a dilation of the vessel system. This constitutes measures which are adapted to rapidly stabilize blood pressure. Since these regulations work in both directions, a constant levelling around a specific blood pressure takes place. This regulation process which also takes place at rest becomes apparent in longwave (about 0.1 Hz) blood pressure and heart rate variations.

To measure the baroreflex, a method is usually used in which the blood pressure is increased or reduced by external measures (tilt table, pharmacologically, external pressure onto the carotid arteries, etc.) and the blood pressure and the heart rate are thus continuously measured. The heart rate is then plotted against the blood pressure (one respective value for each heartbeat), and a straight line is interpolated through the correspondingly activated region. The baroreflex sensitivity (BRS) in ms/mmHg then results from the slope.

This method is problematic in that the measurement is in most cases invasive (injection of a medication bolus) and in that further regulation parameters can be changed by the medication or the blood pressure activation itself.

Alternatively, the measurement of the longwave rest regulation may be suitable. Here, a data record for the further analysis is obtained via a continuous ECG and a continuous blood pressure measurement over a period of up to several hours. For this time, the patient is at rest such that only the auto-regulative mechanisms are to be visible. Corresponding correlations between the blood pressure and the heart rate variability can be derived from the variation with time of blood pressure and heartbeat interval values.

A known method to this end is the so-called sequence method. Sequences of at least three consecutive increasing (or decreasing) blood pressure values are here searched for in the blood pressure series. Correspondingly decreasing (increasing) sequences to these sequences are searched for in the heart rate values, either beginning at the same heartbeat or shifted by one or several heartbeats, depending on the model taken as a basis. Slopes are in turn calculated from these associated sequences and are averaged and indicated as BRS values.

The difficulty of this measurement consists in the determination of these sequences. At rest, the underlying regulation mechanisms are poorly pronounced, and the blood pressure variations are low. They can therefore easily be superimposed by noise and are thus not detected. This leads to long measurement times or to statistically not meaningful mean values.

There are further correlation methods in the frequency range of the measured values or on the basis of other correlation parameters between the blood pressure curve and the heart rate, which are however considerably more complicated with regard to calculation and interpolation.

The drawback in the known correlation-based methods is that though the underlying regulation mechanisms have a relatively constant wavelength at rest, they have no coherent phase due to physiological processes. Owing to movement, respiration, cough or similar processes, these regulations may have short "blackouts" of a few heartbeats, which complicates a normal frequency-based correlation analysis.

All aforementioned methods have in common that they require a continuous blood pressure measurement. The continuous heart rate measurement is carried out in an unproblematic manner via a normal ECG lead and the determination of the R waves in the ECG. The heartbeat interval is defined via the time interval of the R waves.

The continuous blood pressure measurement takes place in a non-invasive way, usually by finger cuffs in which the cuff pressure is maintained exactly on the pulse pressure in the finger by a regulation circuit. This is measured by an IR diode which records the pulsatile change in volume. This method has the drawback that due to the constriction on the finger, it is uncomfortable for the patient and can thus not be used over longer time periods. Furthermore, the handling of the finger cuff is laborious due to pressure hoses and additional height correction sensors.

Furthermore, a regular calibration is necessary for the determination of the blood pressure from the cuff pressure. During this calibration, the cuffs are inflated up to a maximum value and released again in intervals during several seconds such that a conventional oscillatory blood pressure measurement can be carried out for calibration. The are no continuous blood pressure data for this period of time, which means that the latter cannot contribute to the measuring. In an extreme case, the blood pressure itself may even be influenced by the intense inflation of the cuff.

The bivariate phase-rectified signal averaging=BPRSA is known from the article "*Bivariate phase-rectified signal averaging—a novel technique for cross-correlation analysis in noisy nonstationary signals*", Journal of Electrocardiology 42 (2009), 602-606, A. Bauer et al. On the one hand, this method describes a so-called phase-rectified averaging in which the (physiological) signals, the phase of which can be interrupted, can again be made available by an appropriate synchronized averaging of the frequency analysis. Furthermore, the ratio between two different synchronously recorded biosignals is observed to describe corresponding correlations. However, the method described here also has the aforementioned drawbacks with regard to the measurement of the blood pressure.

SUMMARY OF THE INVENTION

The invention provides a simple, fast, and robust measurement of the baroreflex activity which can do without the conventional measurement of blood pressure with a cuff.

According to one aspect of the invention, a method and a system for the monitoring and/or measurement of an autoregulation mechanism of the blood pressure of a living being using an ECG signal are provided. The method in particular serves to monitor the baroreflex activity and/or sensitivity (BRS) of the living being. The method advantageously comprises the following steps:
the recording of the ECG signal of the living being,
the recording of a pulse wave curve synchronously (and simultaneously) with the recording of the ECG signal,
the determination of heart rate intervals from the ECG signal,
the determination of a pulse wave transit time for each heart rate interval from the ECG signal (for example from the R wave(s)) and the pulse wave curve,
the determination of a plurality of significant changes in the pulse wave transit times according to a specified criterion,
the selection of one respective heart rate interval correlated in time with each significant change in the pulse wave transit times as an anchor point,
the selection of a determined limited number of temporally successive heart rate intervals temporally before and/or after each anchor point to thus generate a limited sequence of heart rate intervals for each anchor point,
the averaging of the corresponding heart rate intervals of each sequence of a respective anchor point over all sequences of the anchor points.

The present invention thus provides an advantageous, calibration-free, implicit method and system which are based on the fact that merely blood pressure changes from heartbeat to heartbeat are applied on the basis of the change in the pulse wave transit time intervals from heartbeat to heartbeat. Furthermore, only the heart rate intervals are advantageously used.

Generally, an ECG signal of the living being is recorded, and pulse wave transit times are recorded simultaneously therewith. The pulse wave transit time may advantageously occur via a pulse volume detector synchronously in time with the recording of the ECG signal. Furthermore, the heart rate intervals are advantageously determined from the ECG signals. Changes in the pulse wave transit time indicate changes in the blood pressure. So-called anchor points can then be determined in the ECG signal or in the heart rate intervals for significant changes of the blood pressure on the basis of significant changes in the pulse wave transit time between two heartbeats. Finally, the bivariate phase-rectified averaging method (BPRSA) can be applied, and indicator values (BRS) can be determined.

The present method and the system according to aspects and example embodiments of the invention use here anchor points in the course or in a sequence of the heart rate intervals. Starting from these anchor points, windows on the left and on the right side of the thus defined heartbeat or heart rate interval (anchor point) are determined in the course of the heart interval. It is for example possible to select 15 heart rate intervals before and 15 heart rate intervals after the anchor point. In this example, a window of 31 heart rate intervals or heartbeats is obtained with a phase-rectified signal course. A specific interval change between two R waves of successive heartbeats may also be used to select the anchor points.

In order to determine a correlation between the blood pressure change and the heart rate interval, the anchor points are determined from a specific blood pressure change. This is based on the model that an increase in the blood pressure for example, immediately (with a distance of one to two heartbeats) generates a change (decrease) in the heart rate, i.e. an increase of the length/duration of the heart rate interval.

The center of the method is thus the procedure in which the anchor points are not searched for and set in the series of measurements to be examined; rather, the anchor points are determined from another series of measurements, in the present case the blood pressure, the change of which from heartbeat to heartbeat is determined using the pulse wave transit time.

Every time the blood pressure increases from one beat to the next for example, the pulse wave time is smaller than in the previous heartbeat. An anchor point is then set in the heart rate interval exactly at this heartbeat. The averaged phase-rectified curve then indicates the averaged change in the interval duration after a blood pressure increase. It can be read from the curve thus obtained how sharply the heart rate decreases when the blood pressure increases. Depending on the definition of the anchor points, other correlations can also be represented. The complicated non-linear relationships (cf. also the following explanations) between the absolute blood pressure and the pulse wave transit time can thus be ignored.

Due to the averaging over a great number of anchor points, which usually may be 50% of the overall data, it is possible to effectively suppress noise and to use the data in an efficient manner. A signal curve is thus obtained which shows the typical blood pressure-induced resting oscillation of the heart rate change.

The duration of the recording of the ECG signal and of the pulse wave curve is advantageously 10 minutes. However, records of up to several hours can also be carried out.

The advantage according to the invention lies in an integrated system which can do without a cuff-based blood pressure determination, and in a combined and easily operated device which permits the measurement after a comparatively short measurement time. The pulse wave transit time for each heartbeat is used rather than the cuff-based blood pressure measurement. The pulse wave transit time is the time in which the pulse wave generated by the heart systole has progressed up to a pulse wave detector on the finger, for example. The propagation speed of this pulse wave depends on different parameters. The transit time depends, among others, on the vessel stiffness, the distance to the heart, the vessel diameter and also on the systolic blood pressure upon ejection of blood into the body circulation. During a measuring at rest, the physiological parameters such as distance, vessel stiffness, viscosity of blood etc. can be assumed to be constant, only the blood pressure remains as a variable quantity. The exact dependence of the pulse wave transit time on the blood pressure is complex, non-linear and depends on many physiological parameters that are difficult to determine. However, it is always valid that for otherwise constant parameters and an increasing blood pressure, the pulse waves have a higher speed, and vice versa. The pulse wave transit time is therefore exactly inverse to the blood pressure concerning heartbeat-to-heartbeat changes. According to aspects of the present invention, it is advantageously possible to do without the absolute determination of the blood pressure.

It is therefore possible to determine the anchor points with these pure pulse wave transit times using the bivariate phase-rectified averaging method (BPRSA). The absolute values of the blood pressure are unnecessary. The method is thus used in the conventional manner, and a corresponding BPRSA curve is calculated. A BRS index can in turn be determined from the values around the zero point.

According to one aspect of the invention, the method can comprise the detection of R waves in the ECG signal and the determination of the pulse wave transit times using the R waves. It is particularly advantageous that merely the detection of the R waves in the ECG signal is required. It is thus possible to keep low the demands on the device for recording the ECG signal.

To determine the pulse wave transit time, it is further possible to detect the arrival of the pulse wave in the observed pulse volume change. To this end, the so-called foot of the pulse wave can be determined.

The signal curve from the detector (finger clip or patch or hook-and-loop strip having integrated sensors, for example) can be derived twice after filtering and smoothing to determine the foot. The foot is then determined from the maximum of the second time derivation at a distance suitable in time to the R wave and before the maximum of the first time derivation. Appropriate smoothing filters are to be adapted due to noise in the signals and specifically in the derivations.

Alternatively, a corresponding point of the slope can be defined by a mathematical adaptation (least squares) of an appropriate analytical function to the signal portion. In addition to the known adaptations to continuous polynomials at least of degree three, it is also possible to use two partly defined polynomials having different degrees and in which the transition point between the polynomials (or polynomial function)s or another characteristic point represents the foot. These methods are more robust with respect to noise due to appropriate minimization adaptations to the entire signal portion.

A system according to the aspects of the invention may be arranged correspondingly to carry out one or more of the aforementioned mathematical adaptations.

The method can furthermore comprise the determination of the heart rate intervals on the basis of the R waves in the ECG signal. A heart rate interval (RRi) is then determined as a time interval of two successive R waves of two successive heartbeats.

The invention also provides an advantageous system for the monitoring and/or diagnosing of an autoregulation mechanism of the blood pressure in a living being on the basis of an ECG signal.

The system may comprise a device which is arranged so as to record an ECG signal of the living being and to determine heart rate intervals of the living being from the ECG signal. Furthermore, the system may comprise a device including at least one pulse wave sensor.

The system may advantageously be arranged so as to determine of plurality of significant changes (of the same type) in the blood pressure on the basis of changes in the pulse wave transit times (for example beginning at the heart systole up to the pulse wave sensor).

The system may further be arranged so as to determine for each time of a significant change in the pulse wave transit times a anchor point correlated in time (with the changes in the blood pressure) in the heart interval signal. Each anchor point is associated with a heartbeat from the heart interval signal. The selection of the anchor points only occurs with respect to the individual heartbeats which are then advantageously substantially characterized by the R waves.

The heart rate intervals can then be selected from the ECG signal in windows limited in time before and/or after each anchor point (heartbeat, R wave of the heartbeat).

The system can finally be arranged so as to average the heart rate intervals (of these windows) over the plurality of anchor points.

The device for the determination of the heart rate interval can be an ECG system which comprises at least two or only two, preferably three electrodes. As merely the detection of the R wave is important, the ECG system may be set up in a very simple manner.

In this respect, the ECG system can be configured only for the determination of the R waves of the ECG signal. It can further be configured to determine the heart rate intervals on the basis of the R waves.

The device for determining the pulse wave transit time can advantageously comprise an IR diode. The IR diode can be configured to emit light only or at least at a wavelength of approximately 800 nm (in the range of 790 nm to 810 nm, for example). An appropriate IR sensor is then also provided. The IR diode and the corresponding IR sensor can advantageously be accommodated in a finger clip or a strip or patch on the finger such that the finger is transilluminated or illuminated in a transmitting or reflecting manner. Merely volume changes of the blood vessels on the finger for example, are detected here. The change in the blood oxygen saturation then has no influence on the detection of the pulse wave transit times.

The finger clip can advantageously also comprise at least one ECG electrode. In other words, the sensors and the further components for the determination of the pulse wave transit time and at least partly of the ECG signal are then integrated/arranged in a compact sensor or finger clip or hook-and-loop strip.

The system can further comprise a first preamplifier which is configured so as to amplify the signal of the pulse wave sensor, and/or a second preamplifier which is configured so as to amplify signals of ECG electrodes, and/or a prefilter for prefiltering the signals from the pulse wave sensor and the ECG electrodes, and/or an analog-to-digital-converter for the analog-to-digital conversion of the signals from the pulse wave sensor and the ECG electrodes.

Generally, the ECG signal and the pulse wave course are at first recorded synchronously in time. The ECG signal is continuously recorded by at least one respective ECG lead which is connected synchronously time to the pulse wave course sensed simultaneously therewith and corresponding to the respective heart action, and which is recorded by at least one pulse wave sensor at a lead location (a finger, for example) which is arterial with respect thereto. At least one control parameter for example in the form of the heart rate interval is determined therefrom, which is for example obtained from the respective RR intervals (RRi) or the respective pulse frequency. A further control parameter concerning the pressure or volume regulation is determined from the measured pulse wave transit time curves.

The time-synchronous and continuous detection of ECG signals from at least one lead position can be performed in accordance with one of the known lead methods (Frank, Einthoven, Wilson and others) in connection with the leads of the respective arterial pulse curves corresponding to the heartbeat of at least one lead location, wherein appropriate methods for the digital data acquisition and the measurement data processing can be applied.

In the present context, the signal sensing the variation of the pulse wave transit times is also referred to as trigger signal. The heart rate interval signal is referred to as target signal. The determination of the anchor points (also to be referred to as time markers) is, among others, a particularly critical condition for the successful applicability of the method.

In the method according to the invention, threshold values in the form of predetermined signal amplitudes or predetermined slopes of the variation of the pulse wave transit time can be selected as trigger. The trigger may also be determined from an averaging over several, for example the last 3 or 5 heartbeats. The selection of the correspondingly suitable values for a trigger and of the time windows is performed by previous empirical examinations. To exclude defective multiple triggers within the same heart action, the operation can be inhibited for a specific period of time after the first initiation of a trigger (for example the threshold exceedance).

According to the invention, a heartbeat-to-heartbeat change in the blood pressure is therefore detected on the basis of the variation of the pulse wave transit time. Therefore, in the present case, merely the change in the pulse wave transit time from heartbeat-to-heartbeat is used. The absolute blood pressure values need not be determined. This constitutes a considerable improvement with respect to methods and systems which additionally require the absolute blood pressure values. A so-called anchor point within the heart interval signal is identified from the changes in the pulse wave transit time from heartbeat-to-heartbeat. The respective time intervals (heart rate intervals) can thus be identified from the time series with respect to the times of appearance of successive R waves. The variation with time of the occurring, regulation-dependent and significant time differences of successive R-R intervals or heart rate intervals thus characterizes the heart rate variability.

According to a further aspect of the invention, the application of the method according to any of the aspects or example embodiments of the invention and/or the use of a system according to any of the aspects or example embodiments of the invention is provided for the determination of the probability of success of the therapy of the living being, in particular of a human patient, after the renal denervation (RDN).

The renal denervation RDN is the (catheter-based) treatment by injection of autonomous nerve connections from and to the kidney for a treatment in case of a therapy-resistant high blood pressure. However, it became apparent that many patients show an insufficient blood pressure decrease in reaction to this measure. The method and system described here are suitable for the selection of patients which do not react to RDN using BRS indicators.

The BRS indicator described here can also be used as an indicator for the operability of the autonomous cardiac regulation system and can thus be weakened in case of a progressive autonomous neurotherapy as a consequence of diabetes mellitus. Using the method and devices according to the invention, a continuous monitoring of the BRS can take place over several months, for example, and the progression of the autonomous neurotherapy or the course of success of a beginning therapy can thus be measured. To this end, other factors derived from the measured values such as the variation of the heart rate (heart rate variability) or the pulse wave transit time as such may also be used.

BRIEF DESCRIPTION OF THE FIGURES

Further advantages and features of the invention will become apparent from the description below of the preferred example embodiments of the invention with reference to the accompanying figures, which show

DETAILED DESCRIPTION OF THE EXAMPLE EMBODIMENTS

Figure 1:
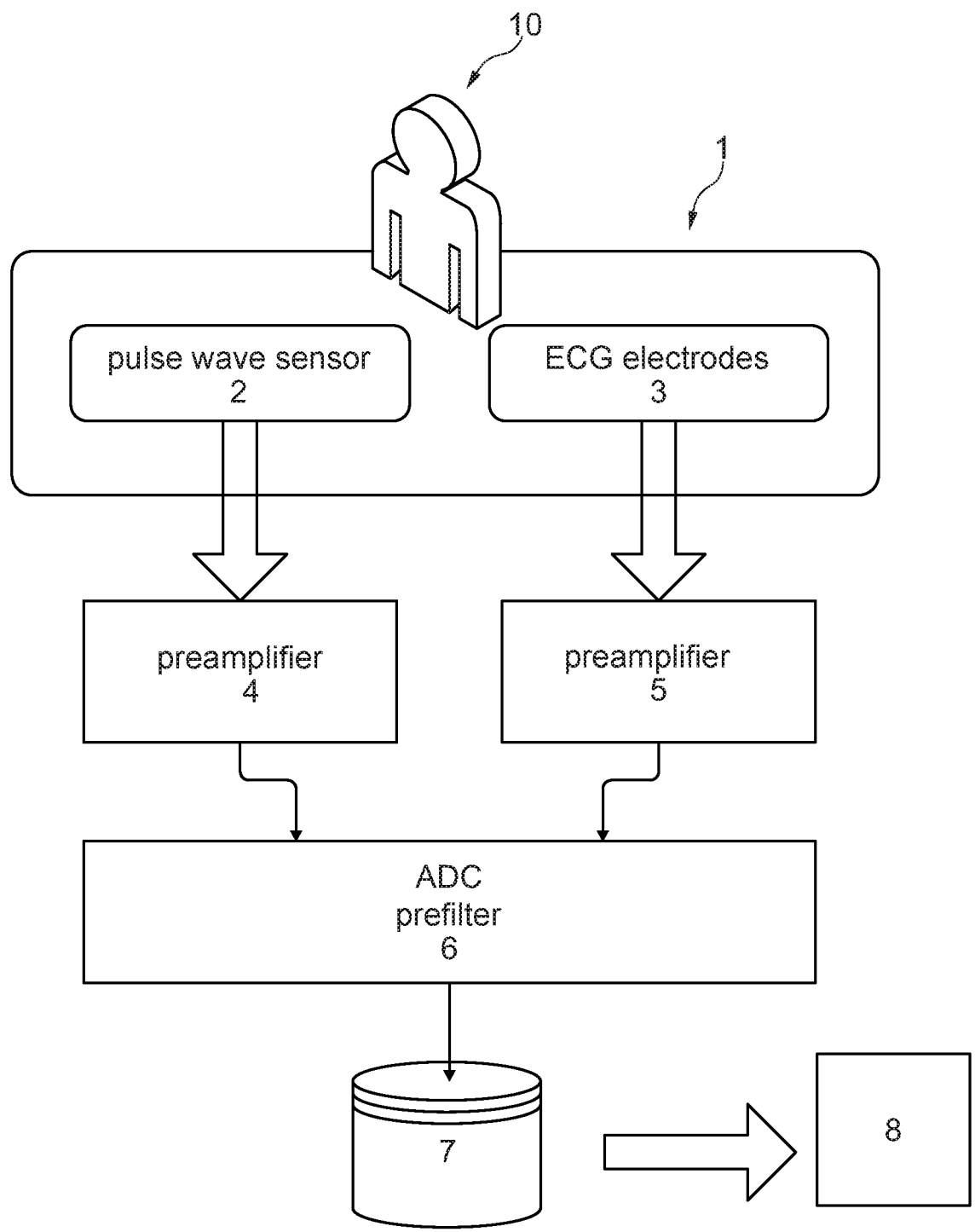
FIG. 1 shows a simplified representation of a system according to an example embodiment of the invention.

FIG. 1 is a simplified representation of a system 1 according to an example embodiment of the invention. The system 1 according to the invention comprises a pulse wave sensor 2, ECG electrodes 3, a first preamplifier 4, a second preamplifier 5, an analog-to-digital converter having an appropriate prefilter 6, and a storage 7. Furthermore, a digital signal processing unit is, for example, also present in the form of a computer 8.

The pulse wave sensor 2 can be configured as a finger clip, an elongated strip, in particular a hook-and-loop strip or a strip having a hook-and-loop fastener, or a patch. It can comprise an IR light-emitting diode and an IR sensor. Advantageously, the IR light-emitting diode can emit light of a wavelength in the range of 790 nm to 810 nm, or approximately 800 nm. The IR sensor can then be configured so as to quantitatively sense light of this wavelength. The pulse wave sensor 2 is then advantageously configured as a pulse volume sensor which merely senses the volume change on the finger.

The finger clip can advantageously also comprise an ECG electrode. This can make the handling considerably easier.

The further processing of the sensed, amplified and possibly filtered and digitized signals, namely of the ECG signal and of the pulse wave signal, is then performed in a computer 8, for example, in accordance with the method described below.

Figure 2:
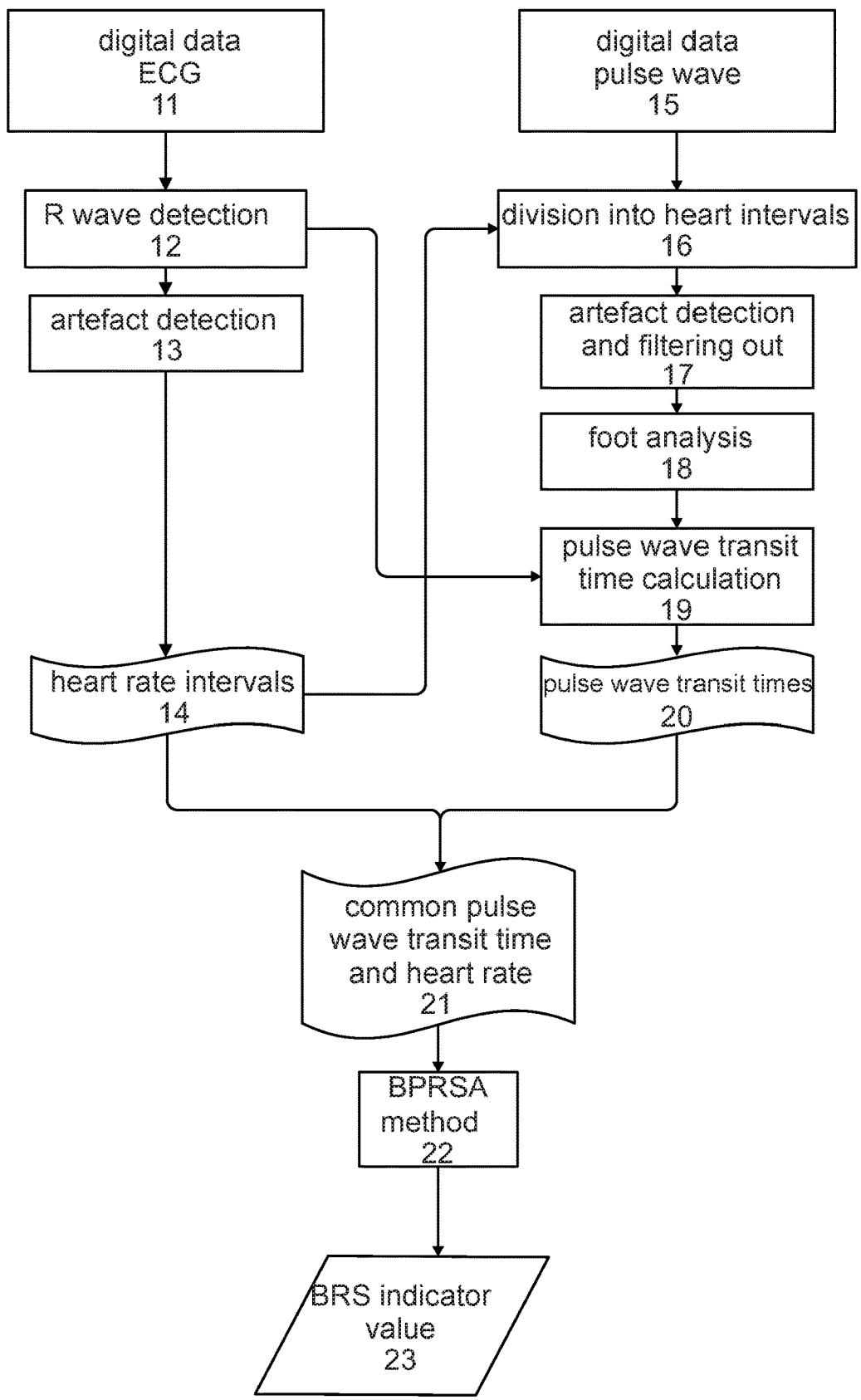
FIG. 2 shows simplified representation of the method according to an example embodiment of the invention using a flow chart, FIG. 3 details an ECG signal and the associated time-synchronous pulse wave course, FIG. 4 details an ECG signal and the associated time-synchronous pulse wave course.

FIG. 2 is a simplified representation of the method according to an example embodiment of the invention using a flow chart. The digital data of the ECG are at first sensed in step 11. The digital data of the pulse wave course are sensed in step 15 simultaneously therewith. In step 12, the R waves are detected within the digital data of the ECG. Advantageously, time markers are set for each position of an R wave or the maximum of the R wave. Furthermore, a detection of artefacts in the digital ECG data is performed in step 13. The R wave detection in step 12 is used simultaneously with the calculation of the pulse wave transit time in step 19. Here, the R wave may for example serve as a starting point, and a foot of the pulse wave course at the pulse wave sensor 2 as a finish point for the period of a pulse wave. After the R wave detection in step 12 and the artefact detection in step 13, the heart rate intervals (RRi) are determined from the digital data of the ECG in step 14. These heart rate intervals are applied to the digital data of the pulse wave from step 15. They are in particular used for the division into heart intervals in step 16. The heart intervals divided in step 16 are submitted to an artefact detection and a filtering in step 17 to suppress the artefacts. The data are then submitted to a foot analysis in step 18. In step 19, the pulse wave transit time is then calculated taking the detected R waves from the ECG signal into consideration. This results in the processed pulse wave transit times which are taken into account in step 20. Common pulse wave transit times and heart rates are determined in step 21 from the stored heart rate intervals in step 14 and the pulse wave transit times in step 20. The methods of the bivariate phase-rectified averaging method (BPRSA) are then applied in step 22. Finally, a BRS indicator is obtained therefrom in step 23.

Figure 3:
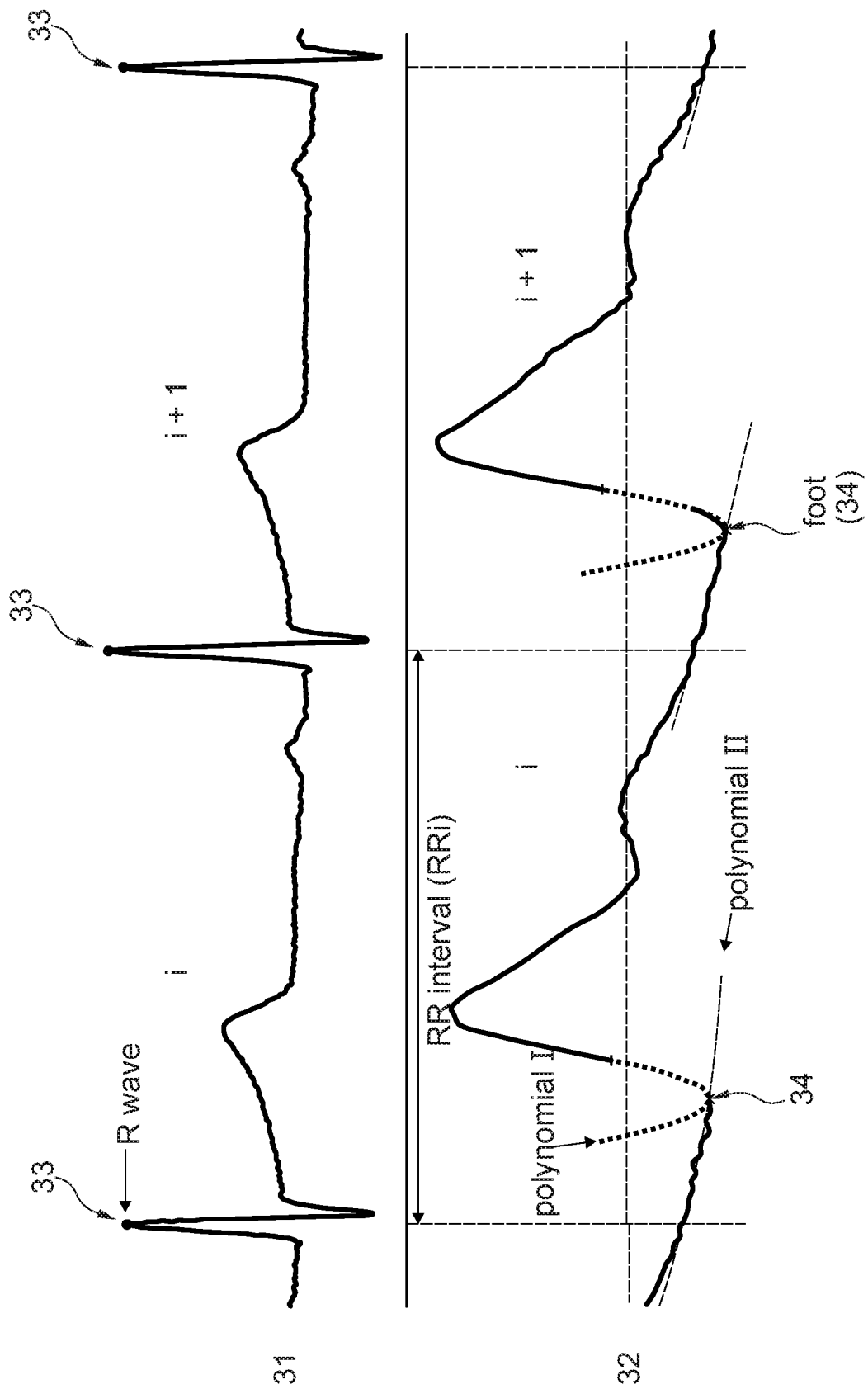
Figure 4:
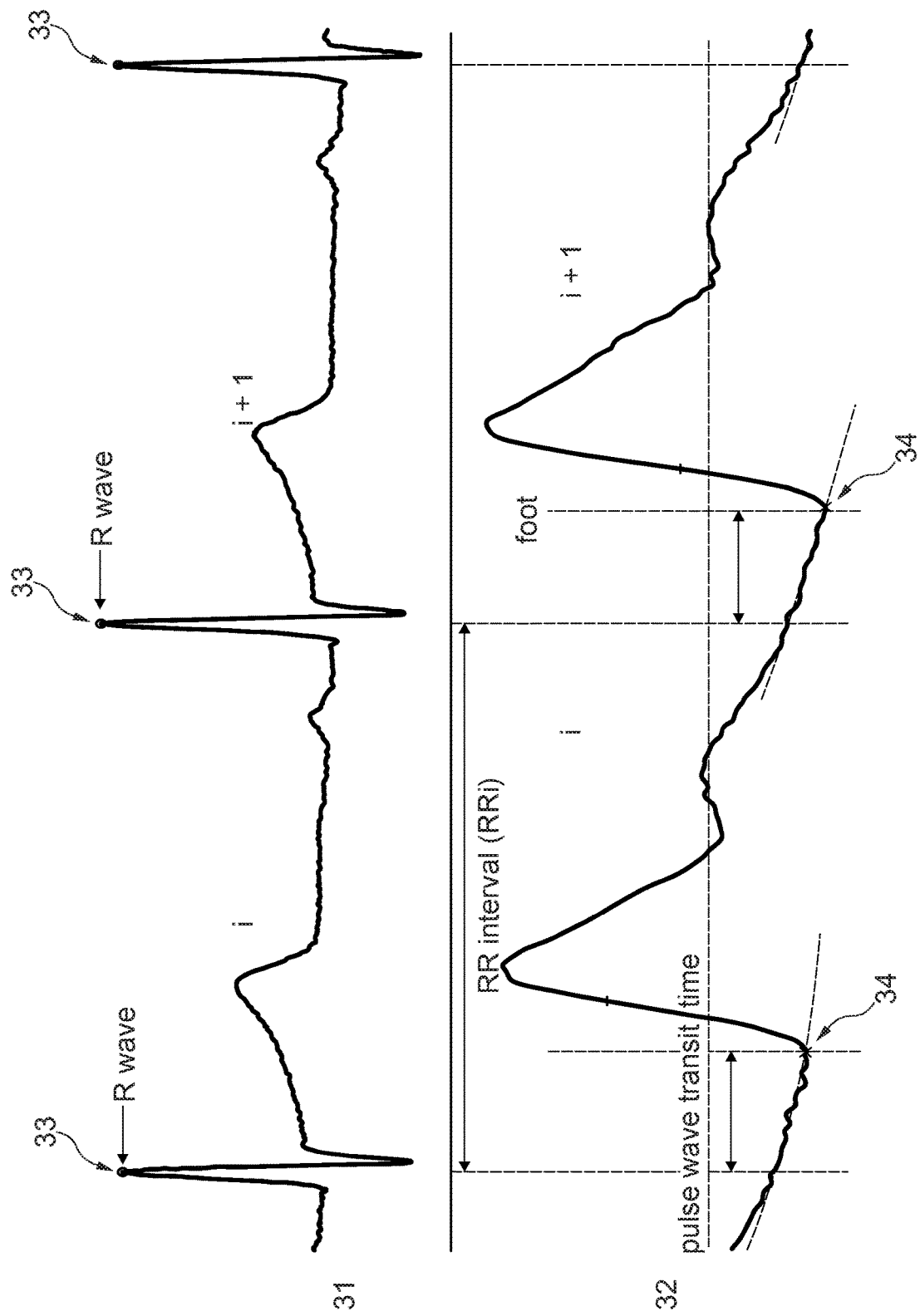

FIG. 3 and FIG. 4 each show a detail from an ECG signal 31 and an associated pulse wave curve 32 recorded synchronously in time for the explanation of the aspects and example embodiments of the invention. According to the methods and devices of the invention and as shown in FIG. 3, the maximum of the R wave 33 for each heartbeat is at first determined on the basis of the ECG signal 31. The time interval between a maximum 33 of an R wave and the next maximum 33 of the next heartbeat is determined therefrom as a heart rate interval (RRi). The pulse wave curve 32 is recorded synchronously in time thereto using the pulse wave sensor and the devices described here. Immediately after the occurrence of an R wave 33, the pulse wave curve first decreases further until it reaches a foot 34 from which it substantially increases again.

As shown in FIG. 4 and according to an example embodiment of the invention, the pulse wave transit time of each heartbeat is now determined as a time interval between the R wave 33, more specifically the maximum of the R wave 33, and the foot 34.

To determine the foot 34, the signal curve from the detector (the finger clip or patch, for example) can be derived twice after the filtering and smoothing. The foot 34 is determined from the maximum of the second time derivation at a distance appropriate in time to the R wave and before the maximum of the first time derivation. For physiological reasons, the distance appropriate in time can be limited as follows, for example:

a) longer than 150 nm, as a certain minimum distance between the finger and the heart (=transit time) can be assumed,
b) less than the last or centre heartbeat interval as a transit time of this length should not occur, even for long extremities, or
c) alternatively it is possible to select a fixed upper limit of 600 ms, for example.

Appropriate smoothing filters are to be used or to be adjusted due to noise in the signals and specifically in the leads.

Alternatively, a corresponding point of the slope can be defined by a mathematical adaptation (least squares) of an appropriate analytical function to the signal portion. In addition to the known adaptations to continuous polynomials at least of degree three, it is also possible to use two partly defined polynomials having different degrees and in which the transition point or another characteristic point represents the foot 34. These methods are more robust with respect to noise due to appropriate minimization adaptations to the entire signal portion.

In this way, it is possible to determine for each heartbeat an associated pulse wave transit time. In case of a significant change in the pulse wave transit time, i.e. in accordance with a previously defined criterion, the associated heartbeat or the associated heart rate interval (RRi) is then selected as an anchor point. Starting therefrom, the temporally successive heart rate intervals lying therebefore and thereafter are selected in a determined quantity. It is for example possible to select, before the heart rate interval i selected as an anchor point, a determined quantity of 15 successive heart rate intervals lying chronologically therebefore. It is also possible to select 15 temporally successive heart rate intervals after the heart rate interval i.

For example, it comes into consideration as a criterion for the selection of a heart rate interval as an anchor point when the pulse wave transit time increases from one heartbeat i to the next heartbeat i+1. Alternatively, it is also possible to suppose a difference of more than one or several milliseconds, for example, as a threshold value for a filtering out of noise effects. However, other criteria which indicate a significant change in blood pressure and can be determined empirically come also into consideration.

On the basis of the selected identical criterion, further heart rate intervals (or also heartbeats) are selected as anchor points in the overall sequence of heartbeats. An averaging is then carried out over all heart rate intervals having the same index, i.e. the corresponding heart rate intervals belonging to the different anchor points.

In case a sequence of selected heart rate intervals RR(k,i) has a number of 31 heartbeats, for example, this sequence then comprises 31 heart rate intervals, namely 15 successive heart rate intervals temporally before the heart rate interval constituting the anchor point, and 15 successive heart rate intervals temporally after the heart rate interval which constitutes the anchor point.

A sequence having number k thus has the heart rate intervals RR(k,i), with i=−m . . . m (here with m=15) and k=1 . . . n. The number m is a positive integer. The number n of the sequences is determined from the number of anchor points and can be between 1 and several hundreds up to several thousands. The figure n is also a positive integer. The heart rate intervals RR(k,i) are averaged over the variable k with a fixed i. i=0 corresponds to the anchor point or the heart interval of the anchor point. The mean value $\overline{RR}_{(i)}$ is therefore calculated as follows:

$$\overline{RR}_{(i)} = \frac{1}{n}\sum_{k=1}^{n} RR_{(i,k)}$$

wherein k denotes the sequence for which an anchor point has been selected, and RR denotes the heart rate interval, i.e. the time from an R wave to the next R wave. As shown by way of example in FIG. 5 for m=15, the $\overline{RR}_{(i)}$ can then be plotted.

Figure 5:
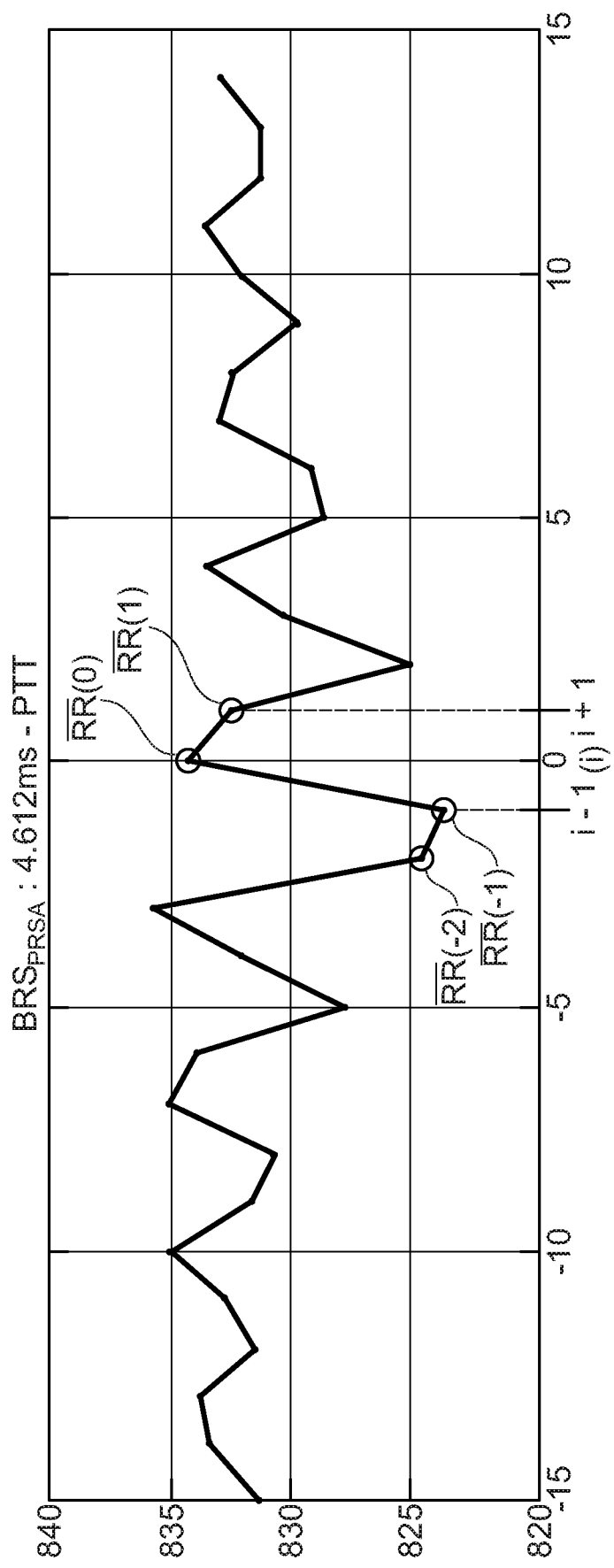
FIG. 5 shows an example for the determination of a BRS indicator.

FIG. 5 shows the result of such an exemplary averaging over 15 heart rate intervals lying before and 15 heart rate intervals lying after the anchor point. As a typical value, approximately 50% of all heart rate intervals may be suitable as anchor point. The number may however be higher or lower depending on the type and number of artefacts. The mean value $\overline{RR}_{(0)}$ of all heart rate intervals i=0 (i.e. anchor points) for k from 1 to n is plotted in the middle, i.e. at the index 0. The mean value $\overline{RR}_{(i+1)}$ of the pulse wave transit times of all heart rate intervals for the index i=1 (i.e. the heart rate interval following the heart rate interval of the anchor point) is plotted next thereto. This is also done for i=1 . . . m. The same procedure is carried out for the heart rate intervals i=1 . . . m lying therefore. The same procedure is also carried out for the heart rate intervals i=−1 ... −m lying therefore. All mean values for the 15 heart rate intervals lying before the anchor point and the 15 heart rate intervals lying after the anchor point are plotted in this way. It must be taken into account that the BRS indicator is a pure time value which does not include any blood pressure value (mmHg). The BRS value 0f 4.612 milliseconds indicated in FIG. 5 then results from:

$$BRS = \frac{1}{4}[\overline{RR}_{(0)} + \overline{RR}_{(1)} - \overline{RR}_{(-1)} - \overline{RR}_{(-2)}]$$

This is the $1^{st}$ coefficient of a Haar wavelet analysis. The calculation of the BRS value from the curve representation is also possible using other methods (such as the slope around the central point or a frequency analysis).

Figure 6:
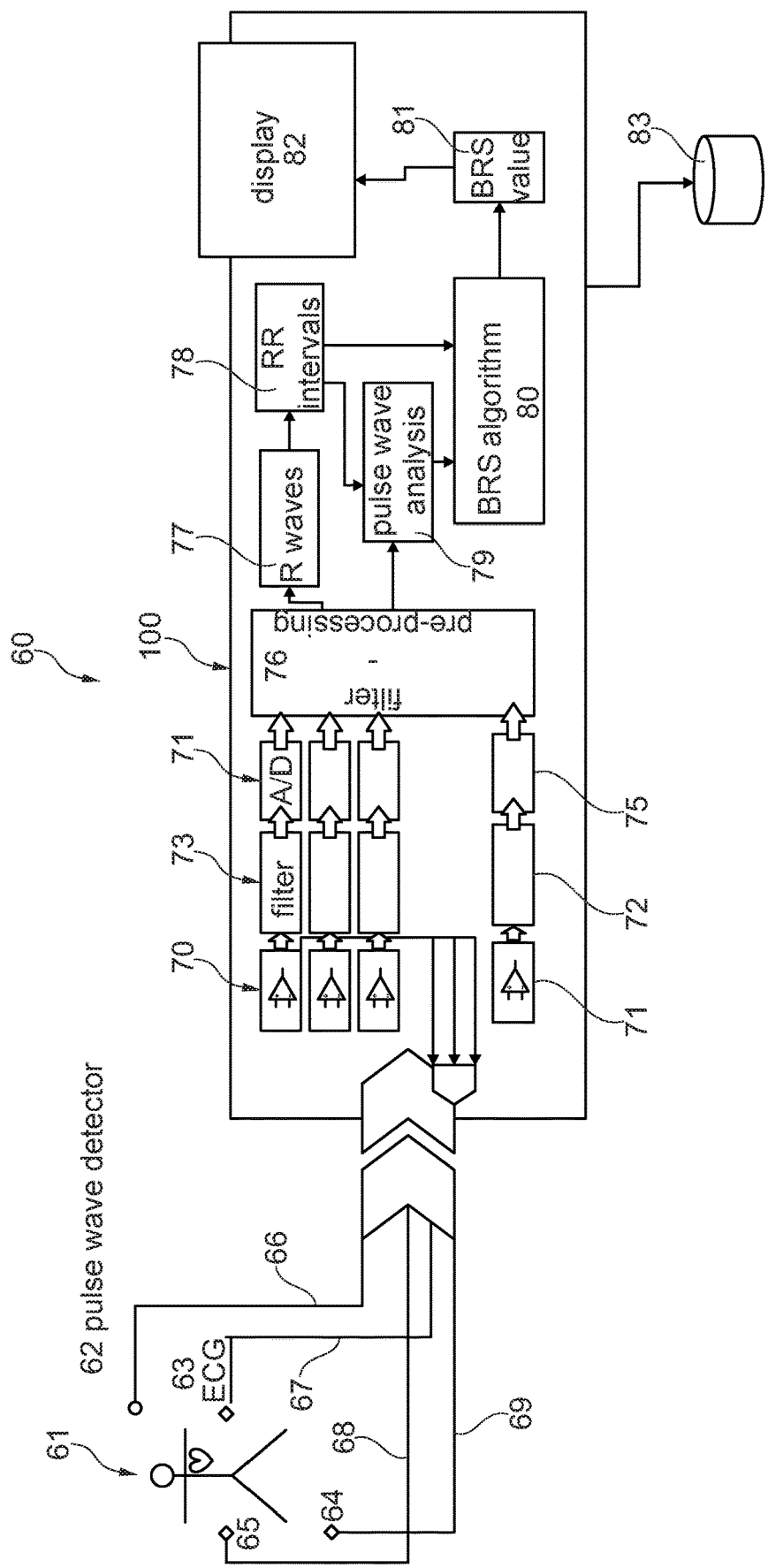
FIG. 6 shows a simplified representation of an example embodiment of a device or a system.

FIG. 6 is a further simplified representation of a device according to the present invention. On the left, there is the test person 61 whose ECG and pulse wave curve are recorded for the determination of BRS values, for example. The device 60 comprises a pulse wave sensor or a pulse wave detector 62, ECG electrodes 63, 64, 65, and an appropriate wiring 66, 67, 68, 69. They are connected to the processing electronics 100. The processing electronics 100 comprise suitable preamplifiers 70, 71 for preamplifying the signals of the pulse wave sensor 62 and of the ECG electrodes 63, 64, 65. The signals from the preamplifiers are usually filtered in the filters 73, 72 and then digitized in analog-to-digital-converters 74, 75. The thus digitized signals are transmitted to a processing unit 76 in which the signals are usually filtered and pre-processed. One the one hand, the R waves of the ECG signal are determined in the unit 76, and on the other hand, a corrected pulse wave curve is output. The heart rate intervals RRi are determined from the R waves in the blocks 76, 77, 78. On the basis of the heart rate intervals of any heartbeat, the associated pulse wave transit times of any heart rate interval are determined in the processing unit 79 for the pulse wave analysis. The heart rate intervals and the results of the pulse wave analysis are forwarded to the processing block 80 in which the algorithm for the determination of the baroreflex sensitivity (BRS) is applied. The baroreflex sensitivity values or indicators (BRS values) 81 are derived therefrom, which can be displayed on a display 82 and/or also be stored in a storage device 83. The BRS values or also other values and signals may of course be subjected to further signal processing measures.

Figure 7:
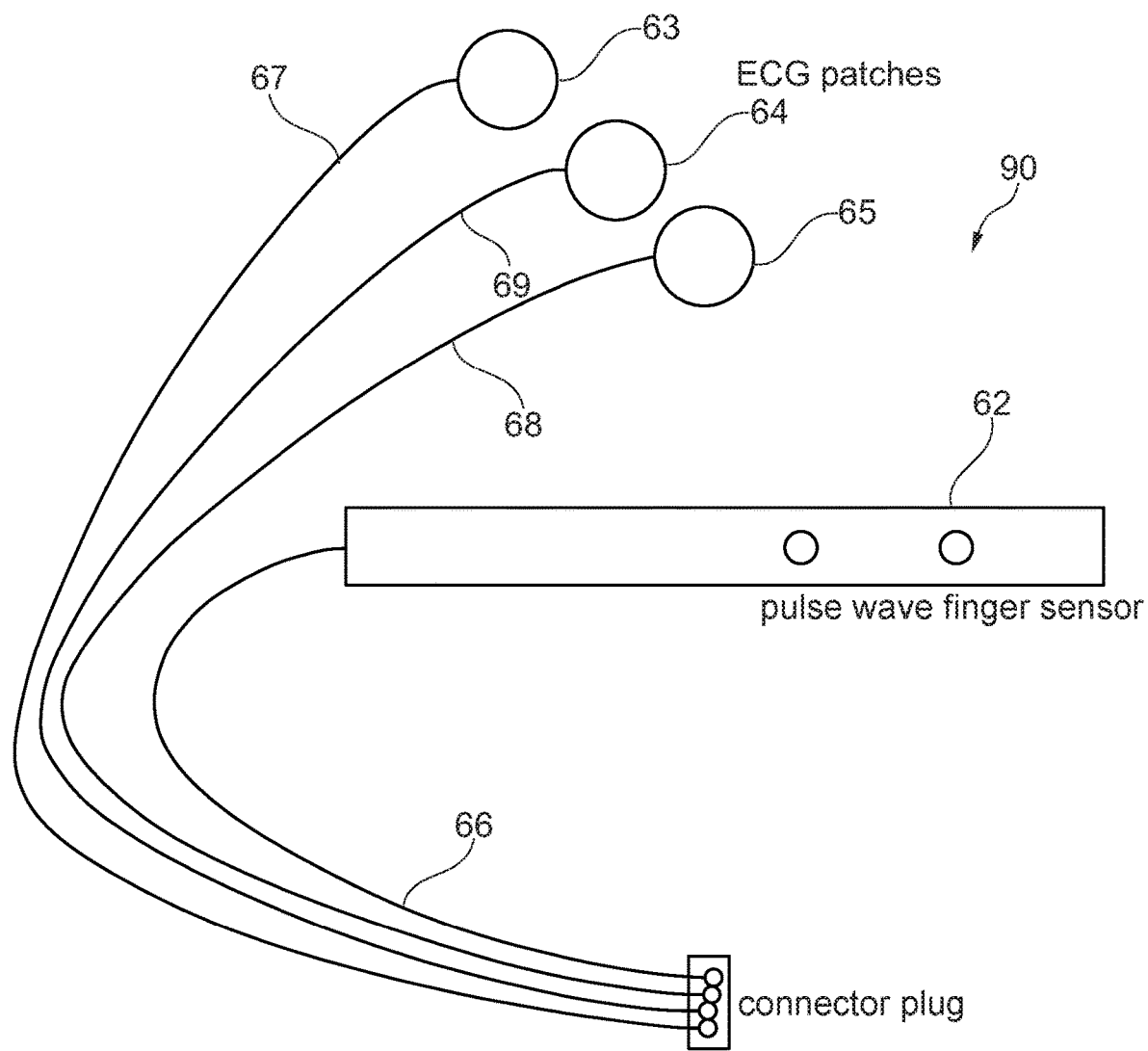
FIG. 7 shows a simplified representation of an example embodiment for the ECG electrodes and the pulse wave sensor.

FIG. 7 shows an example embodiment 90 from which it results that the ECG electrodes 63, 64, 65 have their connecting lines 67, 69, 68 connected to a connector plug which also gets the appropriate wiring to the pulse wave sensor 62. The pulse wave sensor 62 is also represented. In one preferred example embodiment, merely one single connector plug is therefore provided, in which all connecting lines of the ECG electrodes and of the pulse wave sensor 62 are combined mechanically. This may locally simplify the handling of the device.

Figure 8:
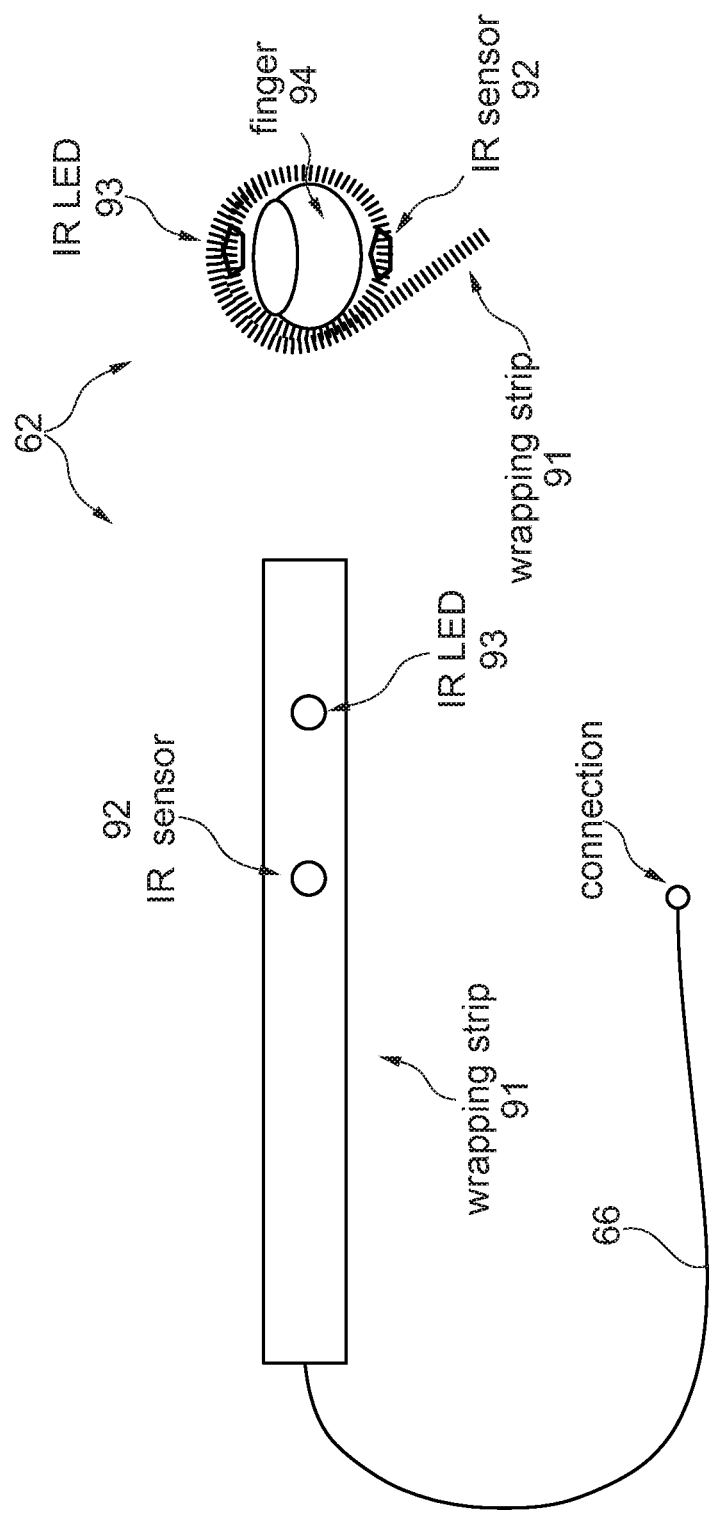
FIG. 8 shows a simplified representation of an example embodiment of the pulse wave sensor.

FIG. 8 shows a simplified representation of the pulse wave sensor 62. This sensor has a wrapping strip or an elongated strap or patch 91. An IR sensor 92 and an IR light-emitting diode 93 are firmly arranged therein. For use, the wrapping strip or the finger sensor 62 are merely wrapped around the finger 94. Due to the dimensions, the IR light-emitting diode 93 and the IR sensor 92 come to rest on opposite sides of the finger 94.

According to the example embodiments and aspects of the invention, extremely efficient, compact and calibration-free as well as robust methods, devices and systems which permit the determination of BRS indicators are all in all provided.

The invention claimed is:

1. A method of monitoring and/or measuring an autoregulation mechanism of blood pressure of a living being using an ECG signal, comprising:
    recording the ECG signal of the living being;
    recording a pulse wave curve synchronously with the recording of the ECG signal;
    providing a digital processing unit adapted to process the ECG signal and pulse wave curve heart rate intervals from the ECG signal;
    using the digital processing unit to determine a pulse wave transit time for each heart rate interval from the pulse wave curve and the ECG signal, in particular from R waves of the ECG signal;
    using the digital processing unit to determine a plurality of significant changes in the pulse wave transit times according to a specified criterion;
    using the digital processing unit to select one respective heart rate interval correlated in time with each significant change in the pulse wave transit times as an anchor point;
    using the digital processing unit to select a determined limited number of temporally successive heart rate intervals temporally before and/or after each anchor point to thus generate a limited sequence of heart rate intervals for each anchor point;
    using the digital processing unit to select to average the corresponding heart rate intervals of each sequence of a respective anchor point over all sequences of the anchor points; and
    using the digital processing unit to determine at least one baroreflective activity and/or sensitivity indicator based on the averaged multiple corresponding heart rate intervals.

2. The method according to claim 1, comprising: determining the heart rate intervals from R waves of the ECG signal, wherein a heart rate interval corresponds to a time between two R waves of successive heartbeats.

3. The method according to claim 1, comprising: detecting R waves in the ECG signal and determining the pulse wave transit time of a respective heartbeat using the R wave and a foot of the pulse wave curve.

4. The method according to claim 3, comprising: defining the foot using a mathematical adaptation, of a "Least Squares" method, and/or of a suitable analytical function to the signal portion to define an appropriate point of a slope which serves as the foot.

5. The method according to claim 4, wherein the mathematical adaptation comprises an adaptation to continuous polynomials at least of degree three, or the mathematical adaptation comprises the use of two partially defined polynomials of different degrees in which a transition point between the polynomials or a different characteristic point represents the foot.

6. The method according to claim 1, wherein the method is used to determine a recommendation of the living being for renal denervation, and/or for the diagnosis and/or therapy of autonomous neurotherapy, in particular determines the success probability of a renal denervation in a living being.

7. The method according to claim 1, providing a digital processing unit to detect a heartbeat-to-heartbeat change in the blood pressure on a basis of variation of the pulse wave transit times without determining absolute blood pressure values, and/or including measuring baroreflex activity and/or sensitivity without measuring blood pressure using a blood-pressure cuff.

8. The method according to claim 1, including using at least one pulse wave sensor to record the pulse wave curve, configuring the at least one pulse wave sensor as a finger clip, an elongated strip, or a patch, and wherein the at least one pulse wave sensor further comprises an IR light-emitting diode and an IR sensor firmly associated with the finger clip, elongated strip, or patch, and providing at least two electrodes of an ECG system to record the ECG signal, and wherein the at least two electrodes have connecting lines connected to one single connector plug which also gets wiring to the at least one pulse wave sensor such that all connecting lines of the at least two electrodes and of the at least one pulse wave sensor are combined mechanically.

9. A system for monitoring and/or diagnosis of an autoregulation mechanism of blood pressure of a living being on a basis of an ECG signal, comprising:
   a first device which is arranged to record an ECG signal of the living being; and
   a second device which comprises at least one pulse wave sensor and which is arranged to record a pulse wave curve,
   the system being further including a digital processing unit that is arranged so as to
      record the ECG signal of the living being using the first device,
      record a pulse wave curve using the second device synchronously with the record of the ECG signal,
      determine heart rate intervals from the ECG signal,
      determine a pulse wave transit time for each heart rate interval from the pulse wave curve,
      determine a plurality of significant changes in the pulse wave transit times according to a specified criterion,
      select one respective heart rate interval correlated in time with each significant change in the pulse wave transit times as an anchor point,
      select a determined limited number of temporally successive heart rate intervals temporally before and/or after each anchor point to thus generate a limited sequence of heart rate intervals for each anchor point,
      average the corresponding heart rate intervals of each sequence of a respective anchor point over all sequences of the anchor points, and
      determine at least one baroreflective activity and/or sensitivity indicator based on the averaged multiple corresponding heart rate intervals.

10. The system according to claim 9, wherein the first device for determining the heart rate interval is an ECG system which comprises at least two electrodes.

11. The system according to claim 10, wherein the ECG system is merely configured for the determination of the R waves of the ECG signal, and the heart rate intervals are determined on the basis of the R waves.

12. The system according to claim 10, wherein the at least one pulse wave is configured as a finger clip, an elongated strip, or a patch, and the at least one pulse wave sensor further comprises an IR light-emitting diode and an IR sensor firmly associated with the finger clip, elongated strip, or patch.

13. The system according to claim 12, wherein the at least two electrodes of the ECG system have connecting lines connected to one single connector plug which also gets wiring to the at least one pulse wave sensor such that all connecting lines of the at least two electrodes and of the at least one pulse wave sensor are combined mechanically.

14. The system according to claim 9, wherein the second device for the determination of the pulse wave transit time comprises an IR sensor and an IR light-emitting diode.

15. The system according to claim 14, wherein the IR light-emitting diode is equipped to emit light at a wavelength of 790 nm to 810 nm, in particular of 800 nm.

16. The system according to claim 14, wherein the IR diode and the IR sensor are accommodated in a finger clip or a patch for a finger or a (hook-and-loop) strip for a finger.

17. The system according to claim 16, wherein the finger clip also includes an ECG electrode.

18. The system according to claim 9, wherein the system further comprises: a first preamplifier which is configured to amplify the signal of the pulse wave sensor, and/or a second preamplifier which is configured to amplify signals of ECG electrodes, and/or a prefilter for prefiltering the signals from the pulse wave sensor and the ECG electrodes, and/or an analog-to-digital-converter for the analog-to-digital conversion of the signals from the pulse wave sensor and of the ECG electrodes.

19. The system according to claim 9, wherein the system determines a recommendation of the living being for renal denervation, and/or for the diagnosis and/or therapy of autonomous neurotherapy, in particular determines the success probability of a renal denervation in a living being.

20. The system according to claim 9, wherein the digital processing unit detects a heartbeat-to-heartbeat change in the blood pressure on a basis of variation of the pulse wave transit times without determining absolute blood pressure values, and/or wherein the system measures baroreflex activity and/or sensitivity without measuring blood pressure using a blood-pressure cuff.

* * * * *